United States Patent
Gurpur et al.

(10) Patent No.: US 12,283,379 B2
(45) Date of Patent: Apr. 22, 2025

(54) AUTOMATIC EARLY PREDICTION OF NEURODEGENERATIVE DISEASES

(71) Applicant: CERNER INNOVATION, INC., Kansas City, KS (US)

(72) Inventors: Praveen Bhat Gurpur, Bengaluru (IN); Kavya Gupta, Bengaluru (IN)

(73) Assignee: Cerner Innovation, Inc., Kansas City, MO (US)

( * ) Notice: Subject to any disclaimer, the term of this patent is extended or adjusted under 35 U.S.C. 154(b) by 365 days.

(21) Appl. No.: 17/119,790

(22) Filed: Dec. 11, 2020

(65) Prior Publication Data
US 2022/0189637 A1  Jun. 16, 2022

(51) Int. Cl.
G16H 50/30 (2018.01)
G16H 10/60 (2018.01)
G16H 50/20 (2018.01)

(52) U.S. Cl.
CPC ............ *G16H 50/30* (2018.01); *G16H 10/60* (2018.01); *G16H 50/20* (2018.01)

(58) Field of Classification Search
CPC ........ G16H 50/30; G16H 10/60; G16H 50/20; G16H 50/70; G16H 70/60; G16H 40/67
See application file for complete search history.

(56) References Cited

U.S. PATENT DOCUMENTS

| | | | | |
|---|---|---|---|---|
| 2003/0040002 A1* | 2/2003 | Ledley | ................... | G16B 40/00 702/20 |
| 2004/0122704 A1* | 6/2004 | Sabol | ...................... | G07C 9/37 706/45 |
| 2007/0061393 A1* | 3/2007 | Moore | ................... | H04L 67/02 709/201 |
| 2007/0118399 A1* | 5/2007 | Avinash | ................. | G16H 10/60 705/2 |
| 2010/0070455 A1* | 3/2010 | Halperin | ................ | G16B 20/20 706/54 |
| 2014/0074509 A1* | 3/2014 | Amarasingham | ...... | G16H 50/70 705/3 |
| 2015/0154372 A1* | 6/2015 | Soenksen | ............... | G16H 50/30 705/2 |

(Continued)

FOREIGN PATENT DOCUMENTS

| | | | | |
|---|---|---|---|---|
| CA | 2458066 A1 * | 8/2005 | ............ | G06F 17/18 |
| CA | 2812342 A1 * | 4/2013 | ........... | C12Q 1/6883 |

(Continued)

OTHER PUBLICATIONS

Yaddanapudi, Suryanarayana. High-Risk Patient Identification: Patient Similarity, Missing Data Analysis, and Pattern Visualization. University of Cincinnati, 2016 Ann Arbor (Year: 2016).*

*Primary Examiner* — Amber A Misiaszek
(74) *Attorney, Agent, or Firm* — Invoke

(57) ABSTRACT

Methods, systems, and computer-readable media are disclosed herein for automated identification and alerting of neurodegenerative diseases (NDD). Patient information comprising medical history information is accessed. Using the patient information, one or more risk factors and/or symptoms for a NDD are identified. Using the identified risk factors and/or symptoms, a patient with probable risk for developing the NDD is determined. A notification of the probable risk that the patient develops the NDD is provided.

20 Claims, 5 Drawing Sheets

(56) References Cited

U.S. PATENT DOCUMENTS

| | | | | |
|---|---|---|---|---|
| 2015/0315649 A1* | 11/2015 | Whitcomb | ....... | A61B 17/00234 |
| | | | | 436/86 |
| 2018/0068083 A1* | 3/2018 | Cohen | .................... | G16B 40/00 |
| 2020/0214648 A1* | 7/2020 | Freeseman-Freeman | ................... | |
| | | | | A61B 5/7282 |
| 2020/0388385 A1* | 12/2020 | De Los Reyes | ....... | G16H 50/70 |

FOREIGN PATENT DOCUMENTS

| | | | | | |
|---|---|---|---|---|---|
| CA | 3077481 A1 * | 4/2019 | ........... | A61B 5/0015 |
| WO | WO-2006072011 A2 * | 7/2006 | ............. | G16H 50/20 |
| WO | WO-2013070895 A1 * | 5/2013 | ............. | G06Q 10/10 |
| WO | WO-2020118158 A1 * | 6/2020 | ........... | C12N 5/0696 |
| WO | WO-2020245727 A1 * | 12/2020 | ............. | G06N 3/006 |

\* cited by examiner

AUTOMATIC EARLY PREDICTION OF NEURODEGENERATIVE DISEASES

BACKGROUND

Neurodegenerative diseases ("NDDs") are a group of disorders that are characterized by progressive degeneration of the central or peripheral nervous system. NDDs may cause-result in degeneration of both the structure and function of the central or peripheral nervous system of a patient. NDDs may result in symptoms that generally start in the brain or central nervous system and progress to cause sensory or motor deficiencies.

Often, a significant period of time elapses before an existing NDD progresses to the point at which physical and visible symptoms can be recognized and a clinical diagnosis can be made. Since the period of time before an existing NDD is diagnosed is often long, the NDD may already have caused significant degeneration in a patient. The onset of NDDs (e.g., Alzheimer's disease, Parkinson's disease, dementia, Multiple sclerosis, Huntington's disease, etc.) may begin long before clinical manifestations. For example, neural degeneration may begin 10-20 years before sensory or motor deficiencies, such as reduced working memory or body tremors, may be recognized.

Susceptibility to developing a NDD has been linked to various risk factors. Risk factors for NDDs may include environmental factors. For example, environmental factors such as certain occupations, previous injuries, exposure to toxins, pesticides and certain metals increase a likelihood of developing Parkinson's disease and other NDDs. Some environment factors such as diet and exercise may indicate a reduced risk for developing a NDD. In addition to environmental factors, genetic factors and life experience factors may indicate an enhanced risk of developing NDDs.

Once a NDD has been diagnosed or suspected in a patient, steps may be taken to treat the disorder. In some cases, the degeneration caused by a NDD may be arrested or slowed with proper medical intervention. In some other cases, physical symptoms caused by NDDs may be alleviated with proper diagnosis and medical treatment.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present disclosure is defined by the claims as supported by the Specification, including the Detailed Description.

It would also be highly desirable to have a system that identifies patients with an enhanced risk of developing or having already developed an unrecognized NDD based on known risk factors and medical records. One aspect of the present disclosure relates to a method for automated identification and alerting of NDDs. Patient information comprising medical history information is accessed. Using the patient information, one or more risk factors for a NDD and/or one or more symptoms of the NDD, are identified. Using the identified risk factors and/or symptoms, determine that a patient associated with the patient information has a probable risk for developing the NDD. A notification is provided of the probable risk that the patient develops the NDD.

In another aspect, the present disclosure relates to a non-transitory computer-readable storage medium having instructions embodied thereon, the instructions being executable by one or more processors to perform a method for automated identification and alerting of NDDs. Patient information comprising medical history information is accessed. Based on the patient information, one or more risk factors to a NDD is determined. Based on the patient information determining where there is one or more symptoms associated with the NDD. Identifying that a patient associated with the patient information has a probable risk for developing the NDD by analyzing the risk factors and symptoms. An indication that the patient has the probable risk of developing the NDD is provided.

In yet another aspect, the present disclosure relates to a system for automated identification and alerting of NDDs. A database comprising electronic medical record ("EMR") data that comprises medical information associated with one or more patients is accessed. Using the EMR data, one or more risk factors for a NDD and/or one or more symptoms of the NDD that are above a threshold risk probability indicative of an enhanced risk for developing the NDD are identified. Using the identified risk factors and/or symptoms, patients who are associated with the risk factors and/or symptoms that are above the threshold risk probability for developing the NDD are identified. A notification is provided to the identified patients.

BRIEF DESCRIPTION OF THE DRAWINGS

Illustrative aspects of the present invention are described in detail below with reference to the attached drawing figures, and wherein.

DETAILED DESCRIPTION

Figure 1:
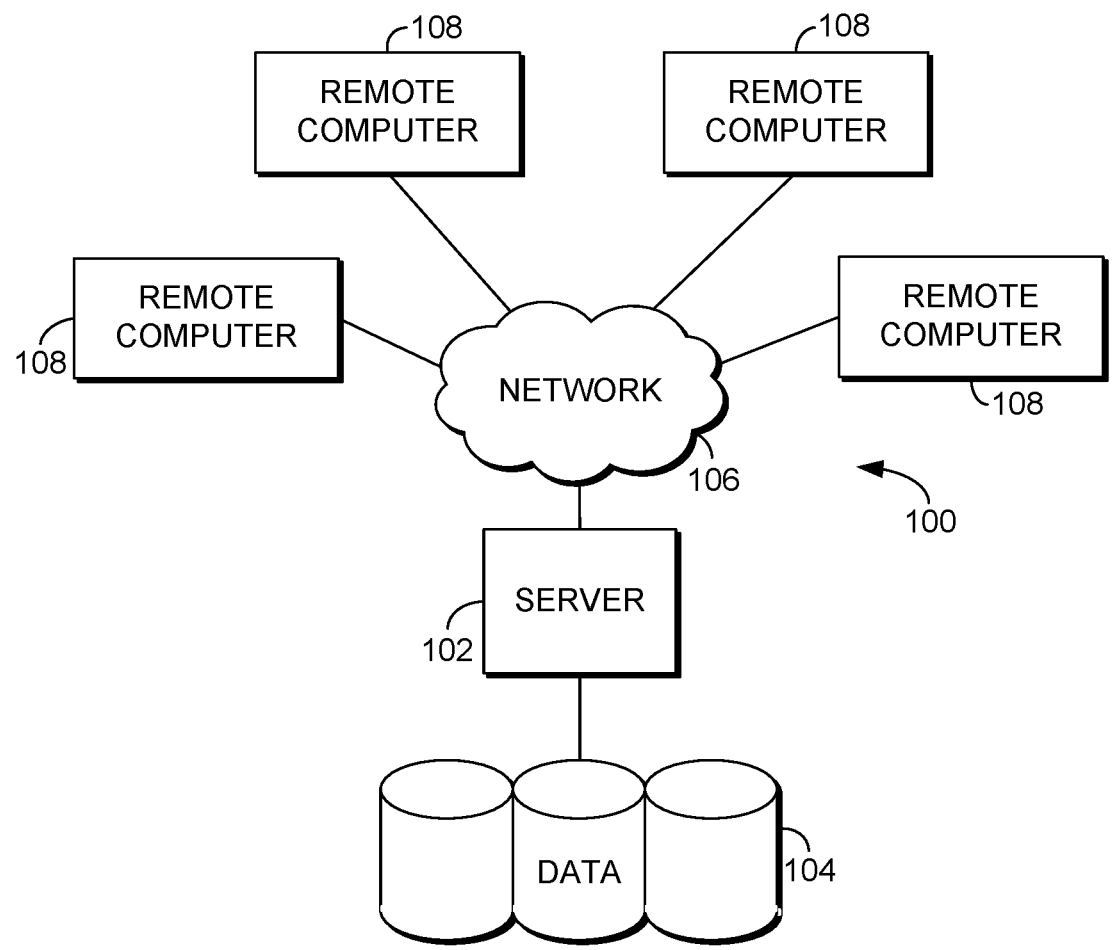
FIG. 1 illustrates a computing environment, in accordance with aspects.

The subject matter of the present invention is being described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Terms should not be interpreted as implying any particular order among or between various steps herein disclosed unless and except when the order of individual steps is explicitly described. As such, although the terms "step" and/or "block" can be used herein to connote different elements of system and/or methods, the terms should not be interpreted as implying any particular order and/or dependencies among or between various components and/or steps herein disclosed unless and except when the order of individual steps is explicitly described. The present disclosure will now be described more fully herein with reference to the accompanying drawings, which may not be drawn to scale and which are not to be construed as limiting. Indeed, the present invention can be embodied in many different forms and should not be construed as limited to the aspects set forth herein. Further, it will be apparent from this Detailed Description that the technological solutions disclosed herein are only a portion of those provided by the present invention. As such, the technological problems, solutions, advances, and improvements expressly referenced and explained herein should not be construed in a way that would limit the benefits, improvements, and/or practical application of the discussed aspects of the present invention.

Accordingly, a system, method, or medium automated identification and alerting of NDDs provides numerous advancements over prior systems, methods, and media. As one example, the present disclosure may access publicly or privately available databases to identify risk factors corresponding to NDDs. As another example, the present disclosure may automatically scan electronic medical record ("EMR") data and identifies people who have high risk factors corresponding to NDDs (e.g., age, occupation, genetic information, family history, clinical test results, etc.) and issues alerts or notifications to those people, caregivers, or medical professionals. These alerts and notifications may provide additional information to the recipient, which may lead to additional medical care (e.g., additional testing, providing additional information, medical advice, diagnosis, etc.) and early recognition and identification of existing NDDs. Early recognition and notification of NDDs may provide reduced symptoms, improved quality of life in patients, and provide significant improvements to the effectiveness and cost of medical treatment.

In addition to improved patient care and treatment, embodiments in the present disclosure reduce burdens on the healthcare system and result in potentially billions of dollars of savings in healthcare expenses. Automated identification and alerting of NDDs provided by embodiments in the present disclosure does not require additional manual efforts, which relieves clinicians and medical professionals from analyzing large quantities of patient records. Additionally, embodiments in the present disclosure may provide an improved determination of a patient's risk of developing a NDD. For example, certain risk factors increase the probability that a person will develop a NDD, but a patient only having one or a few risk factors may still reflect an insignificant risk. In other examples, a patient's information may include several risk factors, that when considered independently, represent only a small risk of developing a NDD, but only when the several risk factors are analyzed in aggregate, do they indicate a heightened risk. For example, a particular patient's exposure to pesticides (i.e., a risk factor for Parkinson's disease) alone may not indicate a significant risk for Parkinson's disease, but if that patient's information also indicates several significant head injuries (e.g., concussions, vehicle crashes, sports injuries, etc.), the analyzed probability of Parkinson's disease may meet a threshold where additional steps or considerations might be taken by healthcare providers.

Additionally, determining the probability of developing a NDD based on many factors that may appear unconnected increases the chances that the patients and healthcare provider will have actual notice of the risk for NDDs in the patient, which may otherwise have gone unrecognized until the NDDs have progressed to be more severe. Patient information may be combined with data from current medical literature and resources to augment or improve the scanning and analysis of patient information. For example, if medical literature proposes a newly identified risk factor for a NDD, this information may be applied to existing patient information. Actual notice of a patient's risk for NDDs enables them to take precautionary measures at early stages (e.g., lifestyle changes, exercise, medication, etc.). Furthermore, alerting or notifying the healthcare professionals may help them to make better informed decisions and to provide improved healthcare services.

Risk factors for NDDs may be grouped into several categories. Risk factors may include environmental factors (e.g., farming activity, well-water, pesticide exposure, solvent exposure, etc.), genetic factors (e.g., family history of NDD, age, mutation, etc.), infectious disease factors (e.g., HIV, Influenza, Diphtheria, etc.), and life experience factors (e.g., head injury, emotional stress, dietary information, etc.). Environmental factors include factors related to exposure to pesticides, metals, solvents or other toxicants. Environmental factors may comprise information indicating direct exposure to toxic materials or may comprise information that indicates a presumed or possible exposure to toxic materials. For example, environmental factors may comprise explicit contact with pesticides or may indicate possible contact from employment in agriculture. Genetic factors comprise factors related to an individual's genetic information. Many NDDs (e.g., Parkinson's disease, Huntington's disease) have been linked to various genetic factors such as a family history of a NDD or particular symptoms. Genetic factors may comprise information related to mutations in specific genes. For example, mutations in the SNCA, Parkin, PINK1, DJ-1, and LRRK2 genes have all been associated with Parkinson's disease. Genetic factors may also comprise information such as aging. Infectious disease factors may comprise information related to infectious diseases that may influence the development of NDDs. Life experience factors may comprise information that relates to a patient's life habits or conditions. For example, life experience factors may include information about a patient's diet, exercise, caffeine consumption, stress, smoking/non-smoking, or any other relevant information. Risk factors for NDDs may be grouped into several categories.

In addition to risk factors, individuals may exhibit symptoms of NDDs. Symptoms may include any measurable or observable indication associated with a NDD. Symptoms may include information measured from a medical or clinical test such as a blood analysis test. In some examples, symptoms may be observable or reported conditions. For example, physical tremors, loss of smell, dizziness, and trouble sleeping are symptoms that have been associated with Parkinson's disease.

Prior systems do not provide such features discussed above. For example, prior systems do not provide preemptive prediction of NDDs in a patient based on analyzing the information in the patient EMR. Further, prior systems do not apply methods for detecting the risk of NDDs based on a patient's risk factors, symptoms, and medical information and do not provide a notification based on the detected risk. Prior systems merely rely on patient-by-patient review of patient records by physicians, neurologists, and other healthcare professionals, which may not be performed quickly or systematically. Additionally, prior systems are reactionary to a diagnosis of NDDs typically after clinical manifestations of the NDDs are observed, rather than early prediction and notification of susceptible patients having high risk factors corresponding to NDDs, where early prediction has the effect of significant prevention and postponement of irreversible damage to a patient's nervous system.

Beginning with FIG. 1, a computing environment 100 that is suitable for use in implementing aspects of the present invention is depicted. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein. Generally, in aspects, the computing environment 100 is a medical-information computing-system environment. However, this is just one example and the computing environment 100 can be operational with other types, other kinds, or other-purpose computing system environments or configurations. Examples of computing systems, environments, and/or configurations that might be suitable for use with the present invention include personal computers, server computers, hand-held or laptop devices, wearable devices, multiprocessor systems, microprocessor-based systems, set top boxes, programmable consumer electronics, network PCs, minicomputers, mainframe computers, distributed computing environments that include any of the above-mentioned systems or devices, and the like.

In aspects, the computing environment 100 can be described in the general context of computer instructions, such as program modules, applications, and/or extensions, being read and executed by a computing device. Examples of computer instructions can include routines, programs, objects, components, and/or data structures that perform particular tasks or implement particular abstract data types. The aspects discussed herein can be practiced in centralized and/or distributed computing environments, i.e., where computer tasks are performed utilizing remote processing devices that are linked through a communications network, whether hardwired, wireless, or a combination thereof. In a distributed configuration, computer instructions might be stored or located in association with one or more local and/or remote computer storage media (e.g., memory storage devices). Accordingly, different portions of computer instructions for implementing the computer tool in the computing environment 100 may be executed and run on different devices, whether local, remote, stationary, and/or mobile.

With continued reference to FIG. 1, the computing environment 100 comprises one or more computing devices in the form of server(s) 102, shown in the example form of a server. Although illustrated as one component in FIG. 1, the present invention can utilize a plurality of local servers and/or remote servers in the computing environment 100. Exemplary components of the server(s) 102 comprise a processing unit, internal system memory, and a suitable system bus for coupling various components, including electronic storage, memory, and the like, such as a data store, a database, and/or a database cluster. Example components of the server(s) 102 include a processing unit, internal system memory, and a suitable system bus for coupling various components, including a data store 104, with the server(s) 102. An example system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The server(s) 102 typically includes therein, or has access to, a variety of non-transitory computer-readable media. Computer-readable media can be any available media that might be accessed by server(s) 102, and includes volatile, nonvolatile, removable, and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

Server(s) 102, in some embodiments, represent a stand-alone computer or computing system, such as a mainframe, blade server, and the like. Alternatively, in some embodiments, the server(s) 102 represent a set of distributed computers, such as multiple cloud computing nodes where data is provisioned or exchanged between the cloud computing nodes. The server(s) 102 might operate in a network 106 using logical connections to one or more remote computers 108. In some aspects, the one or more remote computers 108 can be located at a variety of locations, such as medical facilities, research environments, and/or clinical laboratories (e.g., molecular diagnostic laboratories), as well as hospitals, other inpatient settings (e.g., surgical centers), veterinary environments, ambulatory settings, medical billing offices, financial offices, hospital administration settings, home healthcare environments, and/or clinicians' offices). As used herein, "clinicians," "medical professionals," or "healthcare providers" can include: physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like.

Computer network(s) 106 comprise a local area network (LANs) and/or a wide area network (WAN). Such networking environments are commonplace in offices, enterprise-wide computer networks, intranets, and the Internet. When utilized in a WAN networking environment, the server(s) 102 might comprise a modem or other means for establishing communications over the WAN, such as the Internet. In a networking environment, program modules or portions thereof might be stored in association with the server(s) 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., server(s) 102 and remote computers 108) might be utilized.

The network 106 can include an entity-wide network, campus-wide network, an office-wide network, an enterprise-wide networks, and the Internet. In the network 106, applications, extensions, program modules or portions thereof might be stored in association with the server(s) 102, the data store 104, and any of the one or more remote computers 108. For example, various application programs can reside on the memory associated with any one or more of the remote computers 108. In the computing environment 100, which is illustrated as being a distributed configuration of the network 106, the components and devices can communicate with one another and can be linked to each other using a network 106. It will be appreciated by those of ordinary skill in the art that the network connections shown are exemplary and other means of establishing a communications link between the computers (e.g., server(s) 102 and remote computers 108) might be utilized.

In operation, an organization might enter commands and information, for example, directly in peer-to-peer or near-field communication, or through the network 106 using telecommunications or Wi-Fi. Other input devices comprise microphones, satellite dishes, scanners, or the like. Commands and information might also be sent directly from a remote healthcare device. In addition to a screen, monitor, or touchscreen component, remote computers 108 might comprise other peripheral output devices, such as speakers and printers. Further, in aspects where the network 106 is distributed in configuration, the one or more remote computers 108 may be located at one or more different geographic locations (e.g. located across various locations such as buildings in a campus, medical and research facilities at a medical complex, offices or "branches" of a banking/credit entity, or can be mobile devices that are wearable or carried by personnel, or attached to vehicles or trackable items in a warehouse, for example).

Turning to the data store 104, the data store 104 may be implemented using multiple data stores that are communicatively coupled to one another, independent of the geographic or physical location of a memory device. The data store 104 may also be implemented using a single data store component or may be in the cloud. The data store 104 can, for example, store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. The data store 104 can, for example, also store data in the form of electronic records, such as electronic medical records of patients, patient-specific documents and historical records, transaction records, billing records, task and workflow records, chronological event records, and the like. Generally, the data store 104 includes physical memory that is configured to store information encoded in data. For example, the data store 104 can provide storage for computer-readable instructions, computer-executable instructions, data structures, data arrays, computer programs, applications, and other data that supports the functions and actions to be undertaken using the computing environment 100 and components shown in the example of FIG. 1.

As shown in the example of FIG. 1, when the computing environment 100 operates with distributed components that are communicatively coupled via the network 106, computer instructions, applications, extensions, and/or program modules can be located in local and/or remote computer storage media (e.g., memory storage devices). Aspects of the present invention can be described in the context of computer-executable instructions, such as program modules, being executed by a computing device. Program modules can include, but are not limited to, routines, programs, objects, components, and data structures that perform particular tasks or implement particular abstract data types. Although internal components of the devices in FIG. 1 are not illustrated, those of ordinary skill in the art will appreciate that internal components and their interconnection are present in the devices of FIG. 1. Accordingly, additional details concerning the internal construction device are not further disclosed herein. Although many other internal components of the server(s) 102 and the remote computers 108 are not shown, such components and their interconnection are known. Accordingly, additional details concerning the internal construction of the server(s) 102 and the remote computers 108 are not further disclosed herein.

Additionally, it will be understood by those of ordinary skill in the art that the computing environment 100 is just one example of a suitable computing environment and is not intended to limit the scope of use or functionality of the present invention. Similarly, the computing environment 100 should not be interpreted as imputing any dependency and/or any requirements with regard to each component and combination(s) of components illustrated in FIG. 1. It will be appreciated by those having ordinary skill in the art that the connections illustrated in FIG. 1 are also examples as other methods, hardware, software, and devices for establishing a communications link between the components, devices, systems, and entities, as shown in FIG. 1, can be utilized in implementation of the present invention. Although the connections are depicted using one or more solid lines, it will be understood by those having ordinary skill in the art that the example connections of FIG. 1 can be hardwired or wireless, and can use intermediary components that have been omitted or not included in FIG. 1 for simplicity. As such, the absence of components from FIG. 1 should be not be interpreted as limiting the present invention to exclude additional components and combination(s) of components. Moreover, though devices and components are represented in FIG. 1 as singular devices and components, it will be appreciated that some aspects can include a plurality of the devices and components such that FIG. 1 should not be considered as limiting the number of a device or component.

Figure 2:
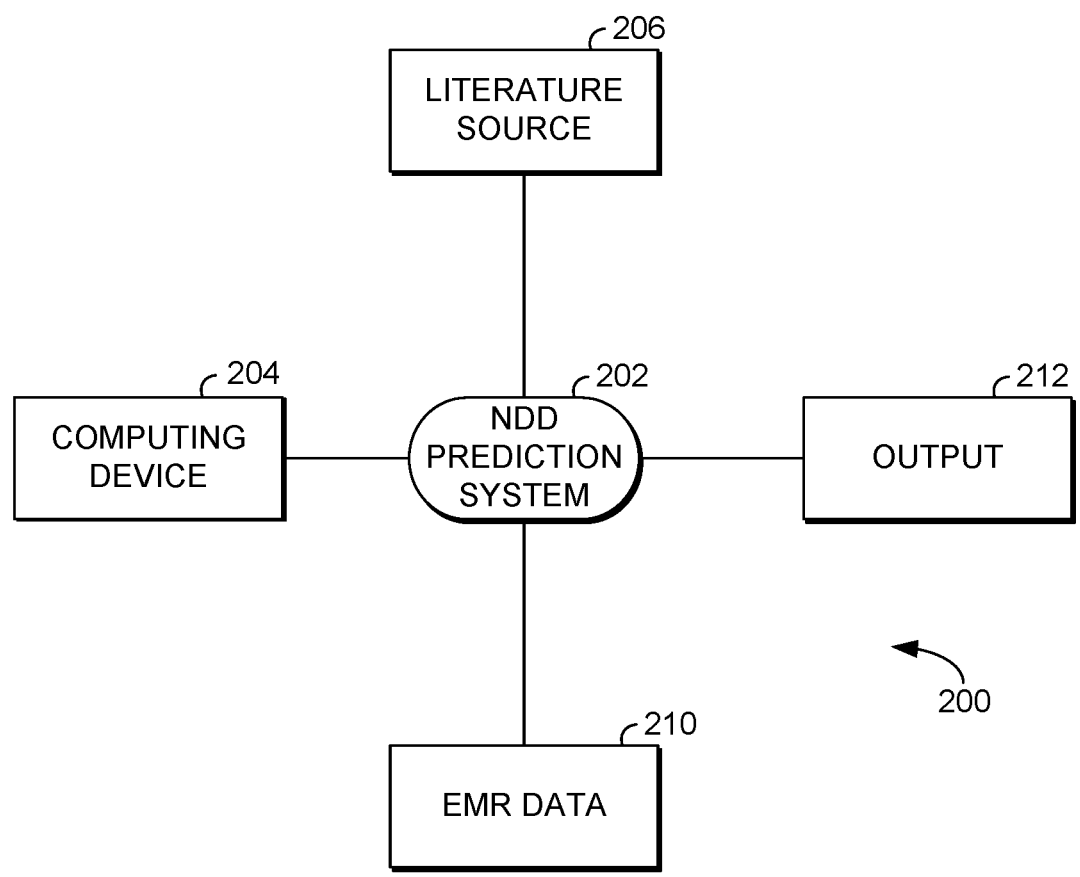
FIG. 2 depicts an exemplary NDD prediction system, in accordance with aspects.

Turning now to FIG. 2, an example of a system is discussed. Example system 200 can be performed via one or more of the devices, components, and/or component interactions previously described in FIG. 1. It should be understood that the methods discussed herein can be implemented or performed via the execution of non-transitory computer-readable instructions and/or executable program code portions stored on computer readable media, using one or more processors. The computer-readable program code can correspond to the application, described above, wherein the application performs the methods, in some aspects. In aspects, the methods can be implemented and performed using a computerized application. As such, the methods may be computer-implemented methods integrated with and executed to complement a computerized clinical workflow.

Example system 200 comprises a NDD Prediction System 202, which is in communication with a computing device 204, a literature source 206, and EMR data 210 from an EMR. Beginning with the computing device 204, computing device 204 may comprise a cell phone, a personal computer, a server computer, other hand-held or laptop devices, a wearable device (e.g. smartwatches, smart eyewear, fitness trackers, smart clothing, wearable cameras, wearable medical devices, etc.), and the like, for example.

Computing device 204 may have healthcare application information that is accessible by the NDD Prediction System. Healthcare application information may include insurance coverage information, scheduled appointments and location of the appointments, medication information about medications being taken (e.g. when a refill is due, where medications are picked up at, whether a medication has not been taken during a period of time), patient task information such as whether an assigned task has been completed and when it was completed, personal health history portals, referral networks, doctor rankings and education, and peer-reviewed disease content, for example.

Turning to the NDD Prediction System 202, the NDD Prediction System 202 may access patient information to determine a probable risk of a NDD. The patient information may be located in EMR data 210 or may be accessed in a plurality of locations.

In some embodiments, some patient information may be located on the computing device 204. The NDD Prediction System 202 uses the patient information to identify one or more risk factors and/or symptoms associated with a NDD. The NDD Prediction System 202 may use any identified risk factors and symptoms to determine a probability or risk that a patient may have, or may develop a NDD. The NDD Prediction System 202 may generate output 212 indicating the determined risk.

The NDD Prediction System 202 may be configured to access patient information related to a particular individual or patient. For example, the NDD Prediction System 202 may access the information of one patient to identify risk factors and symptoms. In some embodiments, the NDD Prediction System 202 may be configured to scan through patient information related to a plurality of patients. For example, the NDD Prediction System 202 may scan through an entire database of patients to detect patients who present significant risk for NDDs. In other examples, the NDD Prediction System 202 may scan though a subset or pre-filtered set of patient information. For example, the NDD Prediction System may only access the patient information of the set of patients that are over the age of 35. The NDD Prediction System 202 may be configured to scan patient information according to a pre-determined frequency so that NDDs may be predicted at periodic intervals. The frequency that patient information is accessed may be determined based on the patient information itself. For example, because age is a significant factor for many NDDs, the patient information related to older patients may be accessed more frequently. In other examples, if a patient information already includes several risk factors or symptoms, this patient information may be accessed more frequently or at a frequency determined based on a previously determined risk.

The NDD Prediction System 202 may identify one or more risk factors and/or symptoms using the patient information. The NDD Prediction System 202 may extract risk factors and/or symptoms from any of a number of data formats and structures in the patient information. In some examples, the risk factors or symptoms may be represented as structured or unstructured data. In some further example, the risk factors or symptoms may be represented as text. The NDD Prediction System 202 may perform analysis on the patient information (e.g. comparisons, natural language analysis, lexical analysis, etc.). In embodiments, a reasoning algorithm may match terms and synonyms within the language of the patient information. In embodiments, a reasoning algorithm may look at temporal or spatial features in the language.

In embodiments, the NDD Prediction System 202 may determine a probability or risk for a patient for a NDD. The probability or risk may be determined based on an algorithm using risk factors or symptoms identified in the patient information. The probability may be a represented as a likelihood that a patient has developed or will develop a NDD. In some embodiments the probability risk may be represented as a score. For example, the NDD Prediction System 202 may determine a risk score generated using the identified risk factors and symptoms. In some embodiments, each of the identified risk factors and symptoms may be weighted to indicate possible contribution to a particular NDD. For example, identified risk factors and symptoms may be weighted against a statistical model for indicating correlation between the factor or symptom and a NDD. In some examples, risk factors and symptoms may be given different weights. The NDD Prediction System 202 may use any algorithm for statistical analysis such as linear regression, Bayesian, Random forest, clustering, etc.

In embodiments, the NDD Prediction System 202 may use an artificial intelligence or machine learning algorithm trained to identify patients at risk for NDDs. Determining a probable risk of a NDD may comprise artificial intelligence logic, such as natural language processing (NLP) based logic, for example, and machine learning logic. This logic may implement a model(s) (e.g. a neural network model, a machine learning model, a deep learning model, etc.). In further embodiments, the NDD Prediction System 202 may usesuse one or more algorithms for differentiating one NDD from one or more other NDDs. For example, the NDD Prediction System 202 may first identify patients at risk for NDDs generally, then may apply an algorithm that further determines a risk for a specific NDD.

In embodiments, the NDD Prediction System 202 may generate the output 212. The output 212 may be generated based on the probability determined by the NDD Prediction System 202. For example, if a patient's risk exceeds a particular threshold risk probability or score indicating high risk for Parkinson's disease, the output 212 may be generated to indicate that this threshold has been exceeded. In other examples, a plurality of thresholds may be used to generate the output. For example, there may be a medium risk threshold and a high risk threshold.

Turning to the literature source 206, literature source 206 may comprise current information on susceptibility and risk factors corresponding to the NDDs. For example, literature source 206 may comprise sources such as PubMed (https://www.ncbi.nlm.nih.gov/pubmed/), World Health Organization (https://www.who.int/), Centers for Disease Control and Prevention (https://www.cdc.gov/), John Hopkins University (https://www.jhu.edu/), Mayo Clinic (http://mayoclinic.org/), and other literature sources using various technologies. In some embodiments, a literature source 206 may also comprise information relating to analyzing risk factors associated with NDDs and predicting NDDs in a patient.

In some embodiments, a selection of the literature source 206 is made for analyzing risk factors associated with a NDD. For example, a literature source 206 from the Centers for Disease Control and Prevention (CDC) can provide data that may provide insight into a newly identified risk factor that may not have previously been included in predicting NDDs. The literature source may indicate a changed or modified weighting or contribution of a risk factor to a particular NDD. For example, a literature source may comprise information suggesting that a risk factor previously thought to have only a slight impact on the risk for a particular NDD may have a more significant impact on the risk determination. In some embodiments, the selection is for sources only related to a particular NDD, while in other embodiments the sources may be related to multiple NDDs, NDDs in general, or any alternative information. In some embodiments, the selection may be restricted to university sources only. In some embodiments, the selection may include a national health source, a global health source, a local health source, and a university source.

Further, the NDD Prediction System 202 may automatically scan the literature source 206. For instance, literature source 206 may be scanned for information relating to particular NDDs and for information relating to susceptibility and risk factors corresponding to the NDD. In some embodiments, a selection of the literature source 206 is made for determining susceptibility and risk factors corresponding to NDDs, wherein determining the susceptibility and risk factors is based in part or solely on the selected literature source(s) 206.

In some embodiments, NDD Prediction System 202 may use cognitive computing to scan the literature source 206 for susceptibility and risk factors corresponding to NDDs. Using the cognitive computing may comprise defining complex analytics in which patterns and trends related to the susceptibility and risk factors are established and generated and can interact with other elements of the NDD Prediction System 202. In some embodiments, using the cognitive computing may comprise communicating with an application programming interface (API) or an application that receives requests from the NDD Prediction System 202 to modify rules for analyzing susceptibility and risk factors. In some embodiments, the cognitive computing may be enriched by context data relating to the NDDs for an in-depth cognitive predictive analytics analysis.

In some embodiments, the cognitive computing comprises artificial intelligence logic, such as natural language processing (NLP) based logic, for example, and machine learning logic, which may be provided as software executed on hardware, specialized hardware, or any combination of the specialized hardware and the executed software. This logic may implement a model(s) (e.g. a neural network model, a machine learning model, a deep learning model, etc.) that may be trained for particular purposes for supporting the particular cognitive operations. Additionally, the logic may implement operations including answering questions, identifying related concepts within different portions of content in a corpus, intelligently searching algorithms (e.g. Internet web page searches), and the like.

In addition, the NDD Prediction System 202 is in communication with an EMR comprising EMR data 210, the EMR including one or more data stores (e.g. data store 104) of health records and one or more computers or servers that facilitate the storing and retrieval of the health records. In some embodiments, the EMR comprising EMR data 210 may be implemented as a cloud-based platform or may be distributed across multiple physical locations. The EMR comprising EMR data 210 may further include record systems, which store real-time or near real-time patient (or user) information, such as wearable, bedside, or in-home patient monitors, for example, and may store patient EMR data 210. For example, the EMR comprising EMR data 210 may comprise one or a plurality of EMR systems such as hospital EMR systems, health information exchange EMR systems, ambulatory clinic EMR systems, or other systems having health-related records for one or more patients.

Generally, EMRs (sometimes referred to as electronic health records (EHRs)), may comprise EMR data 210 comprising electronic clinical documents such as images, clinical notes, orders, summaries, reports, analyses, information received from clinical applications and medical devices, or other types of electronic medical documentation relevant to a particular patient's condition and/or treatment. Electronic clinical documents may contain various types of information relevant to the condition and/or treatment of a particular patient and can include information relating to, for example, patient identification information, images, alert history, culture results, patient-entered information, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information. Further, in some embodiments, EMR data 210 comprising patient data may include patient demographic data, such as age, sex, race, nationality, socioeconomic status, marital status, and employment status and history. This data may further include the patient's insurance information, such as the insurance provider and the type of plan. Additional patient data may include previous and current home and work addresses.

Other types of EMR data 210 comprising patient data include current patient data and historical patient data. In exemplary aspects, current patient data includes data relating to the patient's labs, vitals, diagnoses, medications from a current encounter (e.g., a current admission to a healthcare facility, a current visit to an outpatient facility, or a current period of receiving home healthcare services). The current patient data may include a diagnosis and/or treatment (including medications administered or ordered and procedures performed or ordered). During the current encounter, the patient may be diagnosed or treated with a condition such as asthma, cancer, or heart disease, for example. Current patient data may further include lab results (e.g., physiological data), including vital sign data, from the current encounter. Historical patient data may include information about the patient's past encounters at the current healthcare facility or other healthcare facilities, past encounters at a post-acute care facility, etc. In some embodiments, historical patient data includes previous diagnoses, medications, and lab results. The content and volume of such information in an EMR system are not intended to limit the scope of the present disclosure in any way.

Further, this patient data in the EMR may be received from different sources. In some embodiments, the patient data may be located across a plurality of medical record systems. For example, patient data may be accessed from multiple medical record systems that may be provided by different entities and operated under different standards, services, or interfaces. In some examples, the patient information may be received from one or more public health databases. In some embodiments, data relating to the patient's current condition and/or patient demographics may be received directly from a user, such as the patient or a care provider, inputting such information into a user device. Some current patient data, such as patient variable values, may be received from one or more sensors or monitoring devices or directly from a laboratory running the laboratory procedures. Additionally, historical patient information may be received from the patient's EMR and/or from insurance claims data for the patient. For example, EMR data from in-home care services, hospitals, or any healthcare facility may be received. In an alternative embodiment, the patient's history may be received directly from the patient, such as during registration when admitted to a care facility for the current encounter or starting the current care services (such as with in-home care services).

Turning now to output 212, the output 212 may comprise a notification, an alert, an escalated alert, a message, etc. Output 212 may be sent to patients, clinicians, caregivers, guardians, and the like, in various modes of communication including within healthcare applications and email notifications, short text messages to cell phones, tablets, smart watches, or pagers. In some embodiments, a notification may be provided as a summary of the determinations made by the NDD Prediction System 202. The summary may comprise one or more candidate diagnosis. In some embodiments, output 212 may comprise risk factor and symptom information that may include an indication of risk factors or symptoms detected by the NDD Prediction System 202. In some examples, the risk factor and symptom information may indicate the significance of each of the presented risk factors and/or symptoms. Additionally, the output 212 may also provide information or links related to a detected risk factor or symptom. In some embodiments, the output 212 may include a notification comprising recommendations for additional information or services. In some embodiments, the output 212 may comprise recommendations that suggest additional actions or services. In embodiments, the output 212 may identify services to be performed such as clinical tests or examinations. The output 212 may indicate medical tests or procedures that are related to a diagnosis of a NDD.

Figure 3:
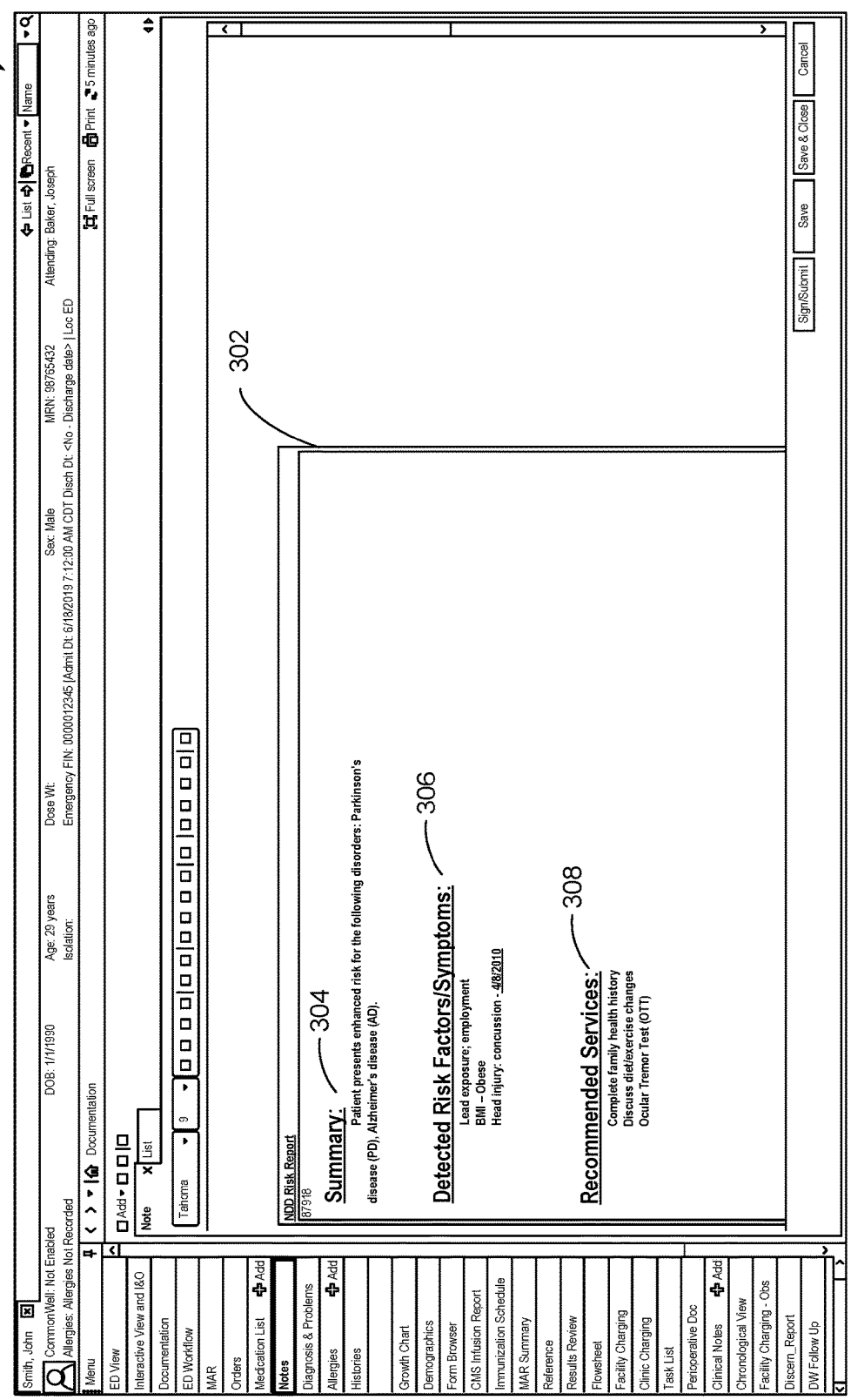
FIG. 3 depicts an exemplary notification environment, in accordance with aspects.

Turning now to FIG. 3, a graphical user interface 300 may display a notification 302. In some embodiments, the notification 302 may indicate that a patient is at risk for developing one or more NDDs. In some embodiments, the notification may be presented as a summary 304 of the determinations made by the NDD Prediction System 202. For example the notification 302, may provide a summary 304302 with a candidate diagnosis such as "Patient presents enhanced risk for the following disorders: Parkinson's disease (PD), Alzheimer's disease (AD)." In some embodiments, the notification 302 may be presented in relation to a single NDD, while in some other embodiments, the notification 302 may be presented in relation to multiple NDDs or other information. In some embodiments, the notification 302 may be presented as related to one single patient. For example, the notification 302 may be presented in relation to patient, "John Smith." In some other examples, the notification 302 may be presented in relation to a plurality of patients. For example, the notification 302 may comprise a listing of a set of patients who exhibit a risk for NDDs. In some embodiments, the notification 302 may indicate the determined risk in addition to a NDD. For example, the notification may indicate that a patient has a greater than 10% chance of developing Parkinson's disease.

In some embodiments, the notification 302 may comprise risk factor and symptom information 306. The risk factor and symptom information 306 may comprise an indication of detected risk factors or symptoms from the patient information. In some examples, the risk factor and symptom information 306 may indicate the significance of each of the presented risk factors and/or symptoms. For example, the risk factor and symptom information 306 may indicate that a patient's age was heavily weighted or considered. In some embodiments, the risk factor and symptom information 306 may comprise a list or ranking of detected risk factors or symptoms that are ordered by significance or some other ranking determination. Additionally, the risk factor and symptom information 306 may also provide information or links related to detected risk factor or symptom. For example, the risk factor and symptom information 306 may include a link to the medical record or report related to a patient's head injury that was identified as a risk factor.

In some embodiments, the notification 302 may comprise recommendations 308, such as recommended information or services. For example, the notification may comprise information relating to Parkinson's disease if it is determined that a patient represents a significant risk for that NDD. In some embodiments, the notification may comprise recommendations 308 that suggest additional actions or services. For example, a notification may comprise a suggestion, prompt, or link for a patient or medical professional to amend, supplement, or complete additional patient information such as a prompt to complete records associated with a patient's family health history. In embodiments, the notification may identify services to be performed. The notification may indicate medical tests or procedures. For example, if a high risk for Parkinson's disease is determined in a patient, it may be suggested in the notification that an Ocular Tremor Test ("OTT") be conducted.

Figure 4:
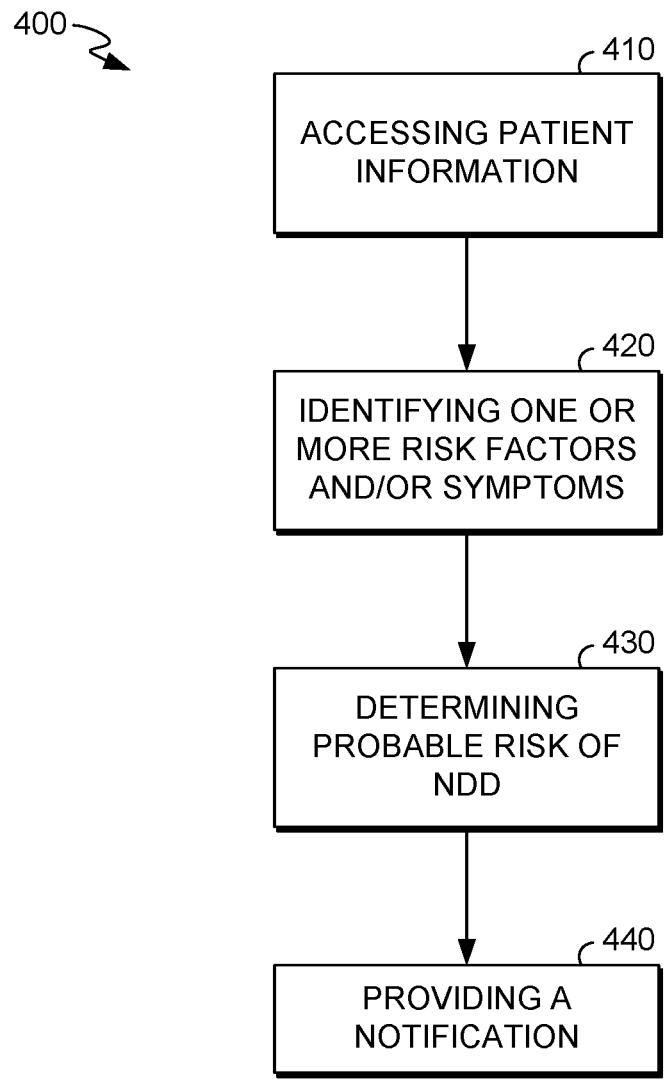
FIG. 4 depicts a flowchart in accordance with aspects of the disclosure.

Turning now to FIG. 4, flow diagram 400 comprises accessing patient information 410, identifying one or more risk factors and/or symptoms 420, determining probable risk of NDD 430, and providing a notification 440. Beginning with accessing patient information 410, the patient information may be accessed from at least one database. In some embodiments, the patient information may be stored on one storage device while in other embodiments, may be located across any of a number of storage devices. For example, the patient information may be located on multiple storage devices connected via a network. The patient information may be represented in EMR data. The EMR data may include patient records and may have structured and unstructured data sources (e.g. EMR data 210 in FIG. 2 discussed above). The structured data sources may include a plurality of databases, such as a laboratory database, a prescription database, and a test result database, for example. The unstructured data sources may include, for example, information in text format (such as treatment notes, admission slips, and reports), image information, and waveform information. In embodiments, patient tracking information may comprise information from an emergency room, a hospital room, a hospice room, an intensive care unit, radiology, etc.

In embodiments, patient information comprising medical history information is automatically scanned. In some embodiments, an EMR is scanned for the patient information. In some embodiments, an EMR and a computing device (e.g. smartphone or smartwatch) are scanned for the patient information and the medical history information. Further, the database may be automatically scanned for risk factors, and symptoms associated with NDDs. For example, patients who have experienced severe head injuries, or other risk factors for Parkinson's disease, may have information related to those injuries saved in the EMR, which may be automatically scanned for information relating to patients with head injuries. In some embodiments, the automatic scanning comprises utilizing cognitive computing, as discussed in FIG. 2. In some embodiments, the patient information relating to a single individual may be accessed, while in other embodiments, patient information relating to any of a number of patients may be accessed.

Turning now to identifying one or more risk factors and/or symptoms 420, the identification of one or more risk factors and/or symptoms may be based on information accessed from patient information or EMR. For example, risk factors may be recorded in patient information or may be determined using the information within the patient information. In some embodiments, risk factors and symptoms related to a single NDD may be identified from patient information, while in other embodiments, risk factors and symptoms related to a group of NDDs may be identified. For example, EMR may be accessed to identify risk factors and symptoms associated with both Parkinson's disease and Huntington's disease. In some examples, a combination of risk factors and symptoms may be identified.

Identifying one or more risk factors and/or symptoms 420, may include determining a risk factor or symptom that is not explicitly recorded in the patient information. For example, exposure to pesticides is a risk factor for several NDDs and a patient information may not indicate an individual's exposure explicitly but exposure to pesticides may be inferred, determined, presumed, or probable based on information that the individual has had long-term employment in the agriculture industry, for example. In other examples, symptoms associated with other conditions, disorders, or diseases may also be identified to be associated with NDD. For example, the symptom of temporary hearing loss may be associated with a diagnosed ear infection in patient information but the loss of hearing may additionally or alternatively be related to a NDD. In embodiments, risk factors for a patient may be identified using the patient information associated with a plurality of patients of the patient information. For example, genetic risk factors may be identified in family members or genetic relatives.

Turning now to determining the probable risk of NDD 430, determining or identifying the probable risk of NDD may be based on the risk that a patient has developed or will develop a NDD based on identified risk factors and symptoms. The probable risk may indicate that a patient has a probability of currently experiencing degenerative effects of one or more NDDs. In some embodiments, the probable risk for a single NDD is determined, while in other embodiments, the risk for multiple NDDs is determined. In some embodiments, the probable risk for NDDs is based on a combination of risk factors, symptoms, and literature sources. For example, a patient's risk for a NDD may be determined using the combination of a risk factor, age, and a symptom, memory loss. In some embodiments the determined probable risk may be recorded or stored in the patient information or on another storage device. For example, the determined risk calculations may be stored in a ledger or log and located in one or more databases within one or more storage devices.

In some embodiments, determining the probable risk of NDD 430 may comprise determining that a risk factor or symptom presents a significant risk in a patient for a NDD. For example, a probability may be calculated to represent the risk for a NDD. In some embodiments, it may be determined that the probable risk of a NDD meets or exceeds a threshold indicating a heightened risk. For example, a probability can be calculated using a patient's risk factors to exceed a particular threshold indicating high risk for Parkinson's disease. In other examples, a plurality of thresholds may be used to determine a plurality of risk levels. For example, a calculated probable risk may exceed a threshold associated with a medium level of risk but may still not exceed another threshold associated with high risk. In some embodiments, determining the probable risk of a NDD 430 may be based on a weighting of the risk factors, symptoms, or any other information used in the determination. Although determining a probability for the risk of a NDD is discussed here, this is not intended to suggest any limitation as to the scope of the invention and any of a number of other suitable methods may be used to determine the risk of a patient for NDDs. For example, a calculated risk score may be determined based on a scoring of a combination of risk factors, symptoms, or any other information. Determining a probable risk of a NDD 430 may comprise artificial intelligence logic, such as natural language processing (NLP) based logic, for example, and machine learning logic. This logic may implement a model(s) (e.g. a neural network model, a machine learning model, a deep learning model, etc.).

Turning now to providing the notification 440, a notification may be provided to at least one computing device of a determined probable risk for a NDD. In embodiments, a notification may be presented in association to a single individual or based on the patient information of a single patient. In some embodiments, a notification related to a plurality of patients may be presented. For example, a listing of patients who are determined to have a high risk corresponding to a NDD. In embodiments, the notification may comprise a representation of an increased risk for a NDD. The representation of the increased risk to the NDD may comprise an indication of the value or severity of a risk for a NDD. For example, the notification may indicate a "High Risk" or "70% Risk" for Parkinson's disease in a patient. In some examples, the notification may include some or all of the risk factors and/or symptoms used to determine the probable risk for a NDD. The notification may indicate the weighting or contribution of a particular risk factor or symptom in calculating the probable risk. For example, the notification may indicate that a patient's age was heavily considered as a risk factor while the patient's weight, while still being a factor, was not given much significance.

The notification may also comprise recommendations, such as recommended information or services. For example, the notification may comprise information relating to Parkinson's disease if it is determined that a patient represents a significant risk for that NDD. In some embodiments, the notification may comprise recommendations that suggest additional actions or services. For example, a notification may comprise a suggestion, prompt, or link for a patient or medical professional to amend, supplement, or complete additional patient information such as a prompt to complete records associated with a patient's family health history. In embodiments, the notification may identify services to be performed. The notification may indicate clinical tests or procedures. For example, if a high risk for Parkinson's disease is determined in a patient, it may be suggested in the notification that an Ocular Tremor Test ("OTT") be conducted. In some embodiments, multiple variations of a notification may be provided. Variations of a notification may be presented based on intended recipient. For example, a notification intended for a medical professional may contain distinct, additional, or more detailed information than a notification intended to be viewed by a patient or caregiver.

Figure 5:
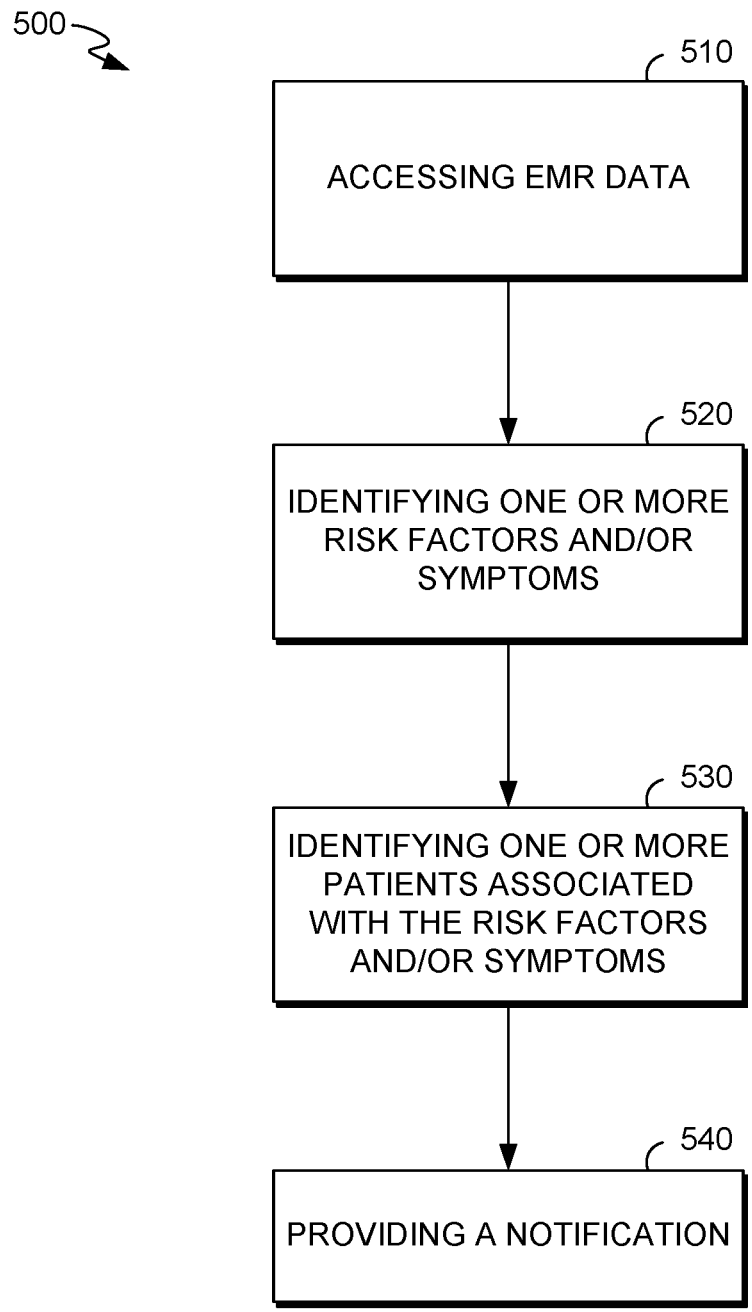
FIG. 5 depicts a flowchart in accordance with aspects of the disclosure.

Turning now to FIG. 5, flow diagram 500 comprises accessing EMR data 510, identifying one or more risk factors and/or symptoms 520, identifying one or more patients associated with the risk factors and/or symptoms 530, and providing a notification 540. Beginning with accessing EMR data 510, the EMR data 510 may be accessed from at least one database. In some embodiments, the patient information may be stored on one storage device while in other embodiments, may be located across any of a number of storage devices. For example, the patient information may be located on multiple storage devices connected via a network. The EMR data may include patient records and may have structured and unstructured data sources (e.g. EMR data 210 in FIG. 2 discussed above). The structured data sources may include a plurality of databases, such as a laboratory database, a prescription database, and a test result database, for example. The unstructured data sources may include, for example, information in text format (such as treatment notes, admission slips, and reports), image information, and waveform information. In embodiments, patient tracking information may comprise information from an emergency room, a hospital room, a hospice room, an intensive care unit, radiology, etc.

In embodiments, EMR data 510 is automatically scanned. Further, the EMR data 510 may be automatically scanned for risk factors, and symptoms associated with NDDs. For example, patients who have experienced severe head injuries, or other risk factors for Parkinson's disease, may have information related to those injuries saved in the EMR, which may be automatically scanned for information relating to patients with head injuries. In some embodiments, the automatic scanning comprises utilizing cognitive computing, as discussed in FIG. 2. In some embodiments EMR data 510 relating to any of a number of patients may be accessed.

Turning now to identifying one or more risk factors and/or symptoms 520, the identification of one or more risk factors and/or symptoms may be based on information accessed from the EMR data 510. In some embodiments, risk factors and symptoms related to a single NDD may be identified from EMR data 510, while in other embodiments, risk factors and symptoms related to a group of NDDs may be identified. For example, EMR may be accessed to identify risk factors and symptoms associated with both Parkinson's disease and Huntington's disease. In some examples, a combination of risk factors and symptoms may be identified.

Turning now to identifying one or more patients associated with the risk factors and/or symptoms 530, identifying one or more patients associated with the risk factors and/or symptoms 530 may be based on the risk that a patient has developed or will develop a NDD based on identified risk factors and symptoms. The probable risk may indicate that a patient has a probability of currently experiencing degenerative effects of one or more NDDs. In some embodiments, the probable risk for a single NDD is determined, while in other embodiments, the risk for multiple NDDs is determined. In some embodiments, the probable risk for NDDs is based on a combination of risk factors, symptoms, and literature sources.

In some embodiments, identifying one or more patients associated with the risk factors and/or symptoms 530 may comprise determining that a risk factor or symptom presents a significant risk in a patient for a NDD. For example, a probability may be calculated to represent the risk for a NDD. In some embodiments, it may be determined that the probable risk of a NDD meets or exceeds a threshold indicating a heightened risk. For example, a probability can be calculated using a patient's risk factors to exceed a particular threshold risk probability indicating high risk for Parkinson's disease. Although identifying one or more patients associated with the risk factors and/or symptoms 530 is discussed here, this is not intended to suggest any limitation as to the scope of the invention and any of a number of other suitable methods may be used to identify one or more patients associated with the risk factors and/or symptoms 530.

Turning now to providing the notification 540, a notification may be provided to at least one computing device of a patient with determined probable risk for a NDD. In embodiments, a notification may be presented in association to a plurality of patients may be presented. For example, a listing of patients who are determined to have a high risk corresponding to a NDD. In some examples, the notification may include some or all of the risk factors and/or symptoms used to determine the probable risk for a NDD.

The present invention has now been described in relation to particular aspects, which are intended in all respects to be illustrative rather than restrictive. Thus the present invention is not limited to these aspects, but variations and modifications can be made without departing from the scope of the present invention.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

The invention claimed is:

1. A method for automated identification and alerting of a neurodegenerative disease (NDD), the method comprising:
   (a) receiving a request at an application programming interface (API) from an automated NDD prediction system to modify a rule for analyzing susceptibility and risk factors;
   (b) responsive to receiving the request: initiating, by the API, a scanning operation of a literature source using cognitive computing to obtain new or changed susceptibility and risk factors corresponding to the NDD, wherein the new or changed susceptibility and risk factors indicate a modified weighting or contribution of a risk factor to the NDD;
   (c) modifying, by a cognitive computing system in communication with the API, a machine learning model based on the modified weighting or contribution of the risk factor to the NDD;
   (d) accessing, by the automated NDD prediction system, patient information comprising medical history information and real-time patient information from a plurality of medical record systems, wherein the patient information (a) comprises structured data and unstructured data and (b) comprises a plurality of data formats;
   (e) identifying, by the automated NDD prediction system, using the patient information and the machine learning model for analyzing patient information, one or more risk factors for the NDD and/or one or more symptoms of the NDD;
   (f) determining, by the automated NDD prediction system, using the identified risk factors and/or symptoms, a probable risk of a patient associated with the patient information developing the NDD and at least one of: a candidate diagnosis, risk factor and symptom information, a link to information related to a detected risk factor or symptom, and an additional action related to a candidate diagnosis;
(g) generating, by the automated NDD prediction system, and formatting for display, a summary based on the determination by the automated NDD prediction system; and
(h) displaying on a graphical user interface, by the automated NDD prediction system, the summary as a notification comprising the probable risk of the patient developing the NDD, wherein a patient is treated based on the notification comprising the probable risk of the patient developing the NDD.

2. The method of claim 1, wherein the risk factor is associated with a weight that reflects an associated contribution of the risk factor to development of the NDD.

3. The method of claim 1, wherein determining that a patient associated with the patient information has a probable risk for developing the NDD is based on one or more machine learning algorithms.

4. The method of claim 1, wherein determining that a patient associated with the patient information has a probable risk for developing the NDD is based on the identified risk factor or symptom exceeding a threshold risk probability.

5. The method of claim 1, wherein the one or more risk factors comprise an environmental factor, genetic factor, infection factor, or life experience factor.

6. The method of claim 1, wherein providing the notification of the probable risk that the patient develops the NDD comprises a notification of the identified risk factors or symptoms.

7. The method of claim 1, further comprising:
identifying, using the patient information, one or more risk factors for a plurality of NDDs;
determining, using the identified symptoms, a candidate diagnosis of a particular NDD of the plurality of NDDs; and
providing an indication of the candidate diagnosis.

8. The method of claim 1, where identifying one or more risk factors for a NDD and/or one or more symptoms of the NDD is further based on accessing one of a public health database, a literature source, or combination thereof.

9. A non-transitory computer-readable storage medium having instructions embodied thereon, the instructions being executable by one or more processors to perform a method for automated identification and alerting of neurodegenerative disease (NDD), the method comprising:
(a) receiving a request at an application programming interface (API) from an automated NDD prediction system to modify a rule for analyzing susceptibility and risk factors;
(b) responsive to receiving the request: initiating, by the API, a scanning operation of a literature source using cognitive computing to obtain new or changed susceptibility and risk factors corresponding to the NDD, wherein the new or changed susceptibility and risk factors indicate a modified weighting or contribution of a risk factor to the NDD;
(c) modifying, by a cognitive computing system in communication with the API, a machine learning model based on the modified weighting or contribution of the risk factor to the NDD;
(d) accessing, by the automated NDD prediction system, patient information comprising medical history information and real-time patient information from a plurality of medical record systems, wherein the patient information (a) comprises structured data and unstructured data and (b) comprises a plurality of data formats;
(e) identifying, by the automated NDD prediction system, using the patient information and the machine learning model for analyzing patient information, one or more risk factors for the NDD and/or one or more symptoms of the NDD;
(f) determining, by the automated NDD prediction system, using the identified risk factors and/or symptoms, a probable risk of a patient associated with the patient information developing the NDD and at least one of: a candidate diagnosis, risk factor and symptom information, a link to information related to a detected risk factor or symptom, and an additional action related to a candidate diagnosis;
(g) generating, by the automated NDD prediction system, and formatting for display, a summary based on the determination by the automated NDD prediction system; and
(h) displaying on a graphical user interface, by the automated NDD prediction system, the summary as a notification comprising the probable risk of the patient developing the NDD, wherein a patient is treated based on the notification comprising the probable risk of the patient developing the NDD.

10. The medium of claim 9, wherein determining whether there is the symptom associated with the NDD is further based on calculating a risk factor score associated with the determined risk factors.

11. The medium of claim 9, wherein analyzing the risk factors and the symptoms is based on a weighting of each of the risk factors and symptoms.

12. The medium of claim 9, wherein the method further comprises:
selecting a frequency for repeating steps (d)-(h) based on the probable risk of the patient developing the NDD; and
repeating steps (d)-(h) at the determined frequency.

13. The medium of claim 9, wherein providing the indication is done via a healthcare application.

14. The medium of claim 9, wherein the patient information is updated upon determining that the patient has a probable risk for developing the NDD.

15. The medium of claim 9, further comprising providing an indication to perform one or more clinical tests associated with the NDD.

16. The medium of claim 9, wherein the NDD is one of Parkinson's disease, Alzheimer's disease, Huntington's disease, dementia, Multiple sclerosis, or a combination thereof.

17. The medium of claim 9, wherein the risk factors comprise at least one of an infectious disease, dietary information, age, genetic information, family history, occupation, or exposure to toxins.

18. A system for automated identification and alerting of neurodegenerative disease (NDD), the system comprising:
one or more processors; and
one or more computer storage media storing computer-useable instructions that, when used by the one or more processors, cause the one or more processors to perform a method, the method comprising:
(a) receiving a request at an application programming interface (API) from an automated NDD prediction system to modify a rule for analyzing susceptibility and risk factors;

(b) responsive to receiving the request: initiating, by the API, a scanning operation of a literature source using cognitive computing to obtain new or changed susceptibility and risk factors corresponding to the NDD, wherein the new or changed susceptibility and risk factors indicate a modified weighting or contribution of a risk factor to the NDD;

(c) modifying, by a cognitive computing system in communication with the API, a machine learning model based on the modified weighting or contribution of the risk factor to the NDD;

(d) accessing, by the automated NDD prediction system, patient information comprising medical history information and real-time patient information from a plurality of medical record systems, wherein the patient information (a) comprises structured data and unstructured data and (b) comprises a plurality of data formats;

(e) identifying, by the automated NDD prediction system, using the patient information and the machine learning model for analyzing patient information, one or more risk factors for the NDD and/or one or more symptoms of the NDD;

(f) determining, by the automated NDD prediction system, using the identified risk factors and/or symptoms, a probable risk of a patient associated with the patient information developing the NDD and at least one of: a candidate diagnosis, risk factor and symptom information, a link to information related to a detected risk factor or symptom, and an additional action related to a candidate diagnosis;

(g) generating, by the automated NDD prediction system, and formatting for display, a summary based on the determination by the automated NDD prediction system; and (h) displaying on a graphical user interface, by the automated NDD prediction system, the summary as a notification comprising the probable risk of the patient developing the NDD, wherein a patient is treated based on the notification comprising the probable risk of the patient developing the NDD.

19. The method of claim 1, wherein the operations further comprise:

selecting a frequency for repeating steps (d)-(h) based on the probable risk of the patient developing the NDD; and repeating steps (d)-(h) at the determined frequency.

20. The method of claim 1, wherein providing the notification comprises sending the notification to a computing device, the notification comprising at least one of: an alert in a healthcare application, an email message, or a text message.

* * * * *